US006353938B1

United States Patent
Young

(10) Patent No.: US 6,353,938 B1
(45) Date of Patent: Mar. 12, 2002

(54) SOUND ATTENUATING EARMUFF

(75) Inventor: Stephen E. Young, Torrance, CA (US)

(73) Assignee: Moldex-Metric, Inc., Culver City, CA (US)

( * ) Notice: Subject to any disclaimer, the term of this patent is extended or adjusted under 35 U.S.C. 154(b) by 0 days.

(21) Appl. No.: 09/854,155

(22) Filed: May 10, 2001

(51) Int. Cl.⁷ .................................................. A42B 1/06

(52) U.S. Cl. ............................ 2/209; 181/129; 381/372

(58) Field of Search ...................... 2/209, 423; 181/129; 381/371, 372, 374, 376, 379

(56) References Cited

U.S. PATENT DOCUMENTS

| 2,684,067 | A | * | 7/1954 | Lienard |
| 3,728,741 | A | * | 4/1973 | Lepor |
| 4,459,707 | A | * | 7/1984 | Stallings |
| 4,674,134 | A | * | 6/1987 | Lundin |
| 5,952,953 | A | * | 9/1999 | Nikawa et al. |

* cited by examiner

Primary Examiner—Rodney M. Lindsey
(74) Attorney, Agent, or Firm—Charles H. Schwartz

(57) ABSTRACT

An earmuff for hearing protection of the ear of a wearer, including an outer cup of rigid plastic material. An inner cup of foam material is supported by the outer cup, and a cushion is attached to the outer cup for lying around the ear of the wearer. The outer cup of rigid plastic material includes a filler of metal powder such as Carbonyl iron powder.

26 Claims, 1 Drawing Sheet

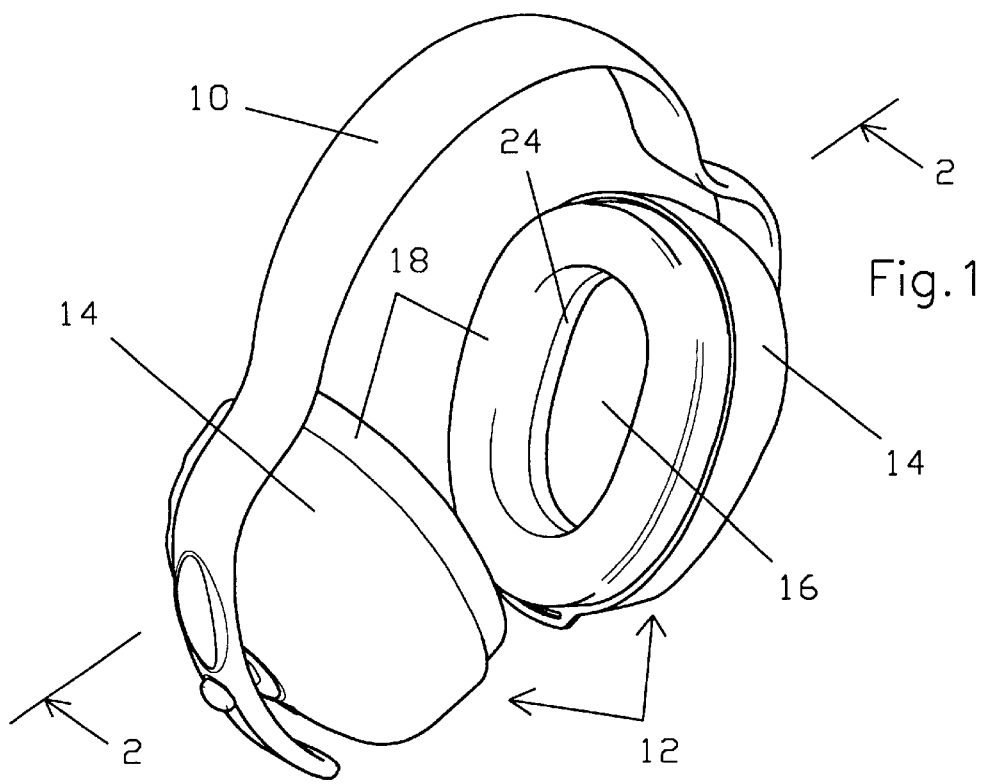
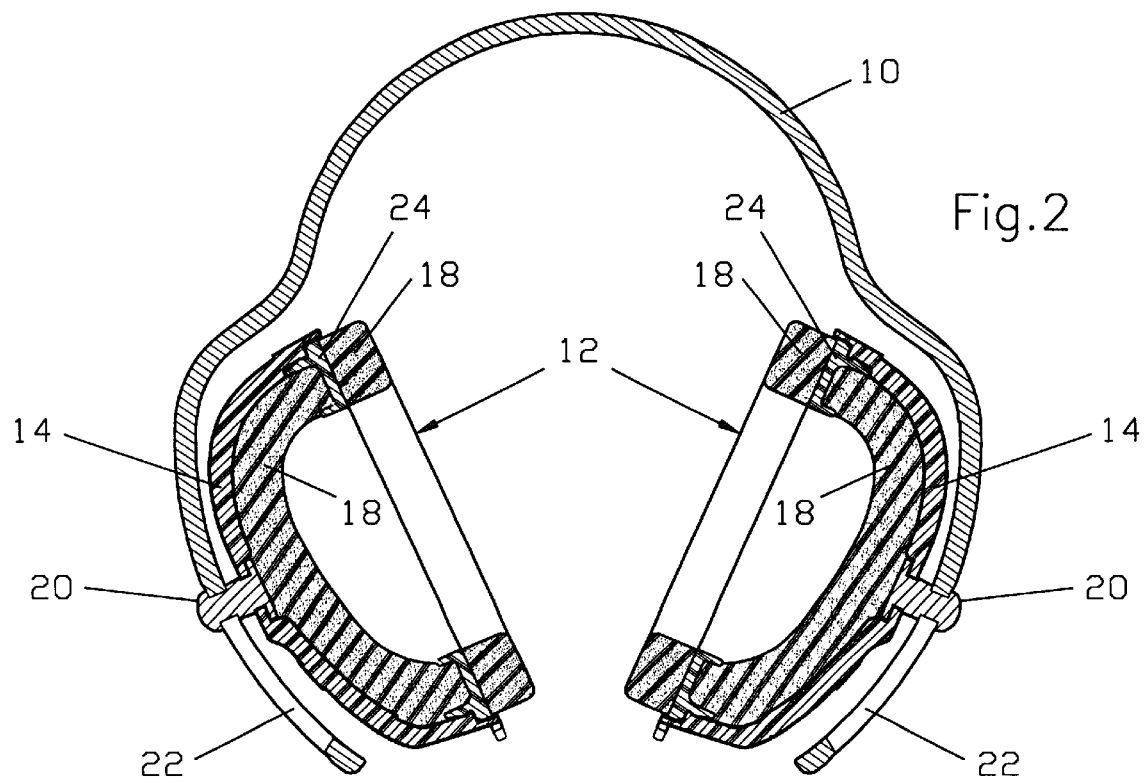

SOUND ATTENUATING EARMUFF

BACKGROUND OF THE INVENTION

Field of the Invention

The present invention relates generally to an earmuff for protecting the ears of a person from noise. In particular the invention is directed to earmuffs of an improved type to provide for additional attenuation of external sound.

In many types of vocations it is necessary for the personnel to be exposed to loud and piercing noises for periods of time. It is therefore desirable to provide for suitable ear protection so as to protect the personnel from any serious or permanent damage to the eardrum.

One type of ear protection that is currently in use are earmuffs, which are comfortable to wear and yet provide suitable protection from ambient noise levels. Typically the earmuffs currently in use are made of a hard outer plastic shell lined with an inner foam cup and with an outer cushion to seal the earmuff around the ear of the user.

In all the various components used to form the earmuff it is desirable to provide for the maximum attenuation consistent with cost and weight.

SUMMARY OF THE INVENTION

In the present invention an earmuff is designed so as to provide for additional attenuation compared to earmuffs of similar design. Additionally, the higher attenuation is achieved using relatively inexpensive materials.

In the prior art the general belief is that in order to achieve a high attenuation the earmuff must have high mass. Because of this, prior art earmuffs have used fairly thick walls for the outer shell or have used higher specific gravity materials in their construction. For example, prior art earmuffs can use a higher price, high specific gravity plastic such as ABS plastic in place of inexpensive polypropylene. In the present invention the earmuff provides for excellent attenuation characteristics with the less expensive plastic polypropylene and also with the use of thinner walls and thereby less plastic material then would generally be used in the prior art.

In the present invention the additional attenuation in the outer cup is achieved by raising the specific gravity of the cup as opposed to making the walls heavier. This results in improved molding and less material. The difficulty with using thicker walls or thicker parts in plastic has a lot to do with the molding of these parts. The thicker the walls the longer the cycle time and the more the molded part can distort. Also the more the part can shrink. In addition, the use of more plastic can significantly increase the cost of the part. The present invention uses a thinner cup wall and increases the specific gravity by including a filler in the plastic.

Unfortunately the use of the standard fillers in increasingly larger amounts does not increase the attenuation, but rather provides for less attenuation. It appears that the addition of the filler makes the cup stiffer as well as heavier. The additional stiffness decreases the attenuation and therefore the use of standard fillers in order to add mass does not achieve the desired results.

The present invention therefore uses a particular type of filler which increases the mass significantly without increasing the stiffness. In addition, the material used as filler is inexpensive in cost and is easy to process in the plastic during the molding. The present invention uses an iron powder incorporated in the inexpensive plastic such as polypropylene. This achieves the desired increase in mass at a relatively low cost without the increase in stiffness.

In particular, a specific Carbonyl iron powder is used to provide for the desired filler material to the plastic. The testing of attenuation for the earmuff using the Carbonyl iron powder included in the plastic cup provided for an increase in attenuation when compared to thicker cups without the iron powder filler. It was therefore determined that the iron powder worked quite well in bringing the attenuation numbers up to a desired level.

It should be appreciated that other types of metal powders could also be used. Iron, however, because it is inexpensive in cost and is inert in use and because it incorporates itself well within the polypropylene, appears to be particularly desirable in use.

A clearer understanding of the invention will be had with reference to the following description and drawings wherein.

BRIEF DESCRIPTION OF THE DRAWINGS

FIG. 1 is a perspective view of an earmuff assembly including a pair of earmuffs supported by a headband to have the earmuffs lie over the ears of user, and FIG. 2 is a cross sectional view of the earmuff assembly taken along lines 2—2 of FIG. 1.

DESCRIPTION

As shown in FIG. 1, the earmuff assembly includes a headband 10 supporting a pair of earmuffs 12 located at opposite ends of the band 10. Band 10 will support the earmuffs 12 to lie on opposite sides of the head of the wearer. Each earmuff 12 covers the ear of the wearer and thereby provides for hearing protection from ambient noises. Each earmuff 12 includes an outer hard plastic cup 14, an inner foam cup 16 and an outer cushion 18. This can be seen in greater detail in the cross sectional view of FIG. 2.

Each earmuff 12 is supported by the headband 10 using a button 20, which is received, in a slot 22 in the headband so as to provide for adjustment of the earmuffs 12 along the side of the head of the wearer. As shown in FIG. 2, the foam cup 16 is supported within the outer plastic cup 14 using a faceplate 24 and with the cushion 18 attached to the faceplate 24. The present invention is concerned specifically with improvements in the composition of the rigid materials used in the earmuff which would include the plastic cup 14 and also the face plate 24. Both of these parts of the earmuff 12 would be composed of a similar hard plastic material.

As described above the present invention includes the use of a specific metal powder filler material added to the plastic for molding into the cup 14 and the face-plate 24. In particular the present invention uses an iron powder, and specifically a Carbonyl iron powder to increase the attenuation of the earmuffs. In particular the attenuation provided by the cup is increased by increasing the mass of the rigid plastic without increasing the stiffness.

The Carbonyl iron powder is unique among iron powders in that it is almost perfectly spherical in shape and is typically made by chemical vapor deposition from pentacarbonyl liquid. The internal structure of the Carbonyl iron spheres is typically a series of layers similar to the layers in an onion. It has been determined that a useful range for the product size in the present application is about 6 microns plus or minus 2 microns.

Another advantage of the Carbonyl iron powder is that it is very pure and only contains trace elements of carbon, oxygen and nitrogen with the rest being iron. In particular the carbon is approximately 0.8%, the oxygen is approximately 0.3% and the nitrogen is 0.8%.

Since the Carbonyl iron powder is almost perfectly spherical in shape this allows the iron powder to fill the plastic very uniformly, as contrasted to other types of non-spherical powder. If the filler is irregular in shape this might not fill the plastic in its molten form in a uniform way. Another advantage in the use of the spherical iron powder occurs during processing of the plastic through a screw or nozzle injector. During the molding the round shape of the iron powder smoothly passes through the screw or nozzle to insure that the mix is both homogenous and the iron is spread evenly throughout the cup. This is an important characteristic since, if the material were not spread uniformly, this could cause variability in the part which could effect the attenuation and thereby degrade the hearing protection.

In the particular mix used in the present invention the mixture includes approximately 10% iron powder, 20% calcium carbonate, 5% carbon black and 0.8% zinc stearate and with the remaining material being straight polypropylene. With this degree of loading of the polypropylene it was found that there would be an increase of a full two DB attenuation compared with a cup that did not include the iron. Using just normal fillers such as the calcium carbonate, it was possible to achieve slight increases in attenuation with filler amounts below 20%, but once the fillers were above 20% the cup would tend to lose attenuation. With the use of the iron, however, it was possible to use the full 20% of the calcium carbonate while increasing attenuation. This would tend to reduce the cost of the cup while achieving the at least two DB increase in attenuation.

It is to be appreciated that various other mixtures may be used and, for example, the increase in attenuation could occur even using smaller amounts of iron such as 5% or greater amounts of iron such as 15%, but that the 10% iron in the particular mix provided for the significant increase in attenuation while also allowing for the use of the filler of relatively inexpensive calcium carbonate up to 20%. Also as indicated above other types of metal fillings could be used, but this could increase the cost and the use of the Carbonyl iron provided for the beneficial results at a relatively low cost.

The particular Carbonyl iron powder used is a product identified by the designation S-1640 and sold by ISP Technologies, Inc. However it is to be appreciated that similar material could be produced by other companies using the chemical vapor deposition from pentacarbonyl liquids.

Although the invention has been described with reference to a particular embodiment, it is to be appreciated various adaptations and modifications maybe made and the invention is only to be limited by the appended claims.

What is claimed is:

1. An earmuff for hearing protection of the ear of a wearer, including
   an outer cup of hard plastic material,
   an inner cup of foam material supported by the outer cup,
     a cushion attached to the outer cup for lying around the ear of the wearer, and the outer cup of hard plastic material mixed with a filler of metal powder.

2. The earmuff of claim 1 wherein the metal powder is iron.

3. The earmuff of claim 1 wherein the metal powder is Carbonyl iron powder.

4. The earmuff of claim 1 wherein the metal powder is in a range between 5 to15% of the total mixture.

5. The earmuff of claim 4 wherein the percentage of metal powder is approximately 10%.

6. The earmuff of claim 4 wherein metal powder is Carbonyl iron powder.

7. The earmuff of claim 6 wherein the percentage of metal powder is approximately 10% Carbonyl iron powder.

8. The earmuff of claim 1 wherein the percentage of metal powder is about 10% iron and with a further filler of about 20% calcium carbonate.

9. The earmuff of claim 8 wherein the hard plastic material further includes 5% carbon black and 0.8% zinc spherate.

10. The earmuff of claim 1 wherein the plastic is polypropylene.

11. The earmuff of claim 10 wherein the filler of metal powder is Carbonyl iron powder in a range between 5 to 15% of the total mixture.

12. The earmuff of claim 11 additionally including a filler of up to 20% calcium carbonate.

13. The earmuff of claim 12 wherein the Carbonyl iron powder is about 10% of the total mixture and the calcium carbonate is about 20% of the total mixture.

14. In an earmuff for hearing protection in the type including a rigid plastic outer cup the improvement including, a filler material for incorporating in the rigid plastic outer cup consisting of metal powder.

15. The earmuff of claim 14 wherein the metal powder is iron.

16. The earmuff of claim 14 wherein the metal powder is Carbonyl iron powder.

17. The earmuff of claim 14 wherein the metal powder is in a range between 5 to 15% of the total mixture.

18. The earmuff of claim 17 wherein the percentage of metal powder is approximately 10%.

19. The earmuff of claim 17 wherein the metal powder is Carbonyl iron powder.

20. The earmuff of claim 19 wherein the percentage of metal powder is about 10% Carbonyl iron powder.

21. The earmuff of claim 14 wherein the percentage of metal powder is about 10% iron and with a further filler of about 20% calcium carbonate.

22. The earmuff of claim 21 further including 5% carbon black and 0.8% zinc spherate.

23. The earmuff of claim 14 wherein the rigid plastic outer cup is formed of polypropylene.

24. The earmuff of claim 23 wherein the filler of metal powder is Carbonyl iron powder in a range between 5 to 15% of the total mixture.

25. The earmuff of claim 24 additionally including a filler of up to 20% calcium carbonate.

26. The earmuff of claim 25 wherein the Carbonyl iron powder is about 10% and the calcium carbonate is about 20% of the total mixture.

* * * * *